| United States Patent [19] | [11] | 4,234,717 |
|---|---|---|
| Tresner et al. | [45] | Nov. 18, 1980 |

[54] ANTIBACTERIAL ANTIBIOTIC BM782

[75] Inventors: Homer D. Tresner, LaFarge, Wis.; Amedeo A. Fantini, New City; Donald B. Borders, Suffern, both of N.Y.; William J. McGahren, Dumont, N.J.

[73] Assignee: American Cyanamid Company, Stamford, Conn.

[21] Appl. No.: 17,000

[22] Filed: Mar. 2, 1979

Related U.S. Application Data

[63] Continuation-in-part of Ser. No. 891,572, Mar. 30, 1978, abandoned.

[51] Int. Cl.$^3$ ...................... A61K 31/71; C07H 15/22
[52] U.S. Cl. .......................... 536/17 R; 260/112.5 R; 424/181; 435/79; 536/4
[58] Field of Search ............................... 536/17, 17 R; 260/112.5

[56] References Cited

U.S. PATENT DOCUMENTS

| 4,071,560 | 1/1978 | Kirby et al. ............................ 536/17 |
| 4,082,735 | 4/1978 | Jones et al. ................... 260/112.5 R |
| 4,091,032 | 5/1978 | Tadanier et al. .............. 260/112.5 R |

*Primary Examiner*—Johnnie R. Brown
*Attorney, Agent, or Firm*—Norton S. Johnson

[57] ABSTRACT

This disclosure describes three new antibiotics designated BM782α1, BM782α2, and BM782α1a which are produced in a microbiological fermentation under controlled conditions using a new strain of an undetermined species of the genus Nocardia or mutants thereof. These new antibacterial agents are active against *Mycobacterium tuberculosis* as well as both gram-positive and gram-negative microorganisms and thus are useful for inhibiting the growth of such bacteria and bacilli wherever they may be found.

3 Claims, 9 Drawing Figures

FIG. 1

INFRARED ABSORPTION SPECTRUM OF BM782α-1 SULFATE SALT IN A KBr DISC

Figure 2:
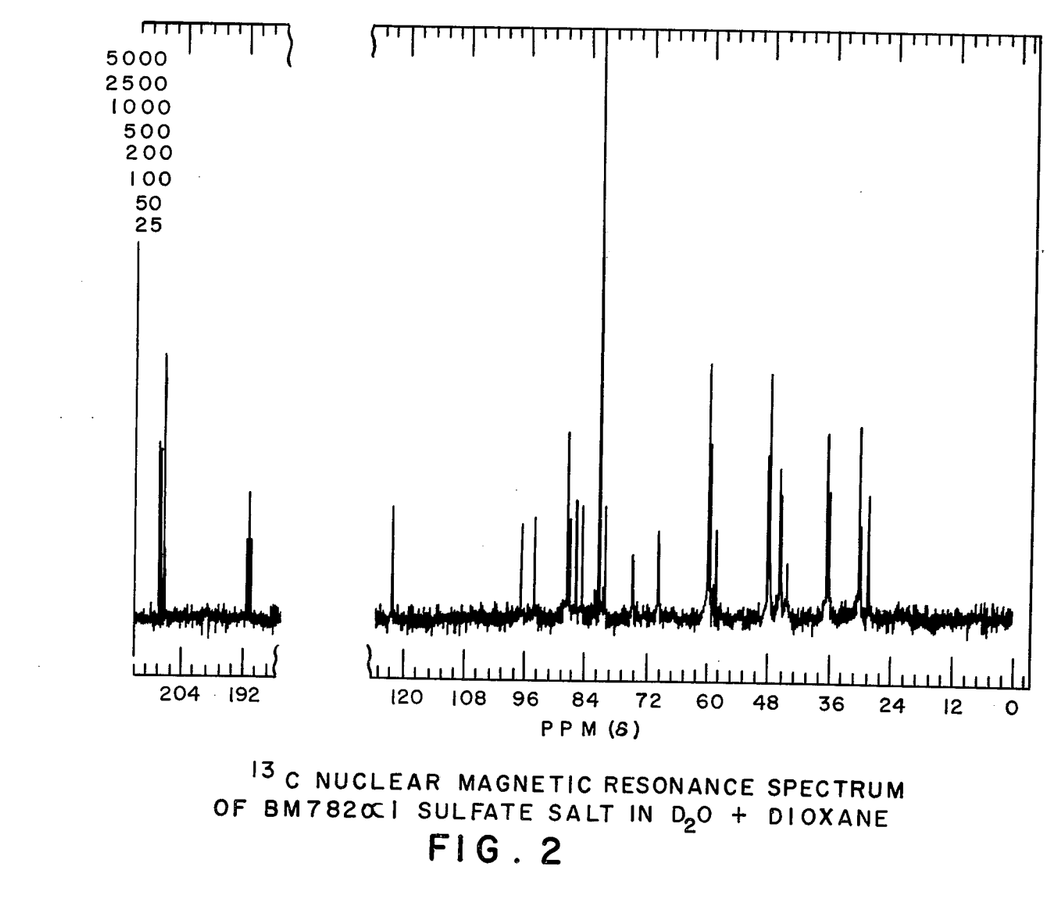

FIG. 2
13C NUCLEAR MAGNETIC RESONANCE SPECTRUM OF BM782α1 SULFATE SALT IN D₂O + DIOXANE

FIG. 4

INFRARED ABSORPTION SPECTRUM OF BM78α2 SULFATE SALT IN A KBr DISC

FIG. 5

$^{13}C$ NUCLEAR MAGNETIC RESONANCE SPECTRUM OF BM782α2 SULFATE SALT IN $D_2O$ + DIOXANE

FIG. 6 PROTON MAGNETIC RESONANCE SPECTRUM OF BM782α2 SULFATE SALT IN D₂O

Figure 7:
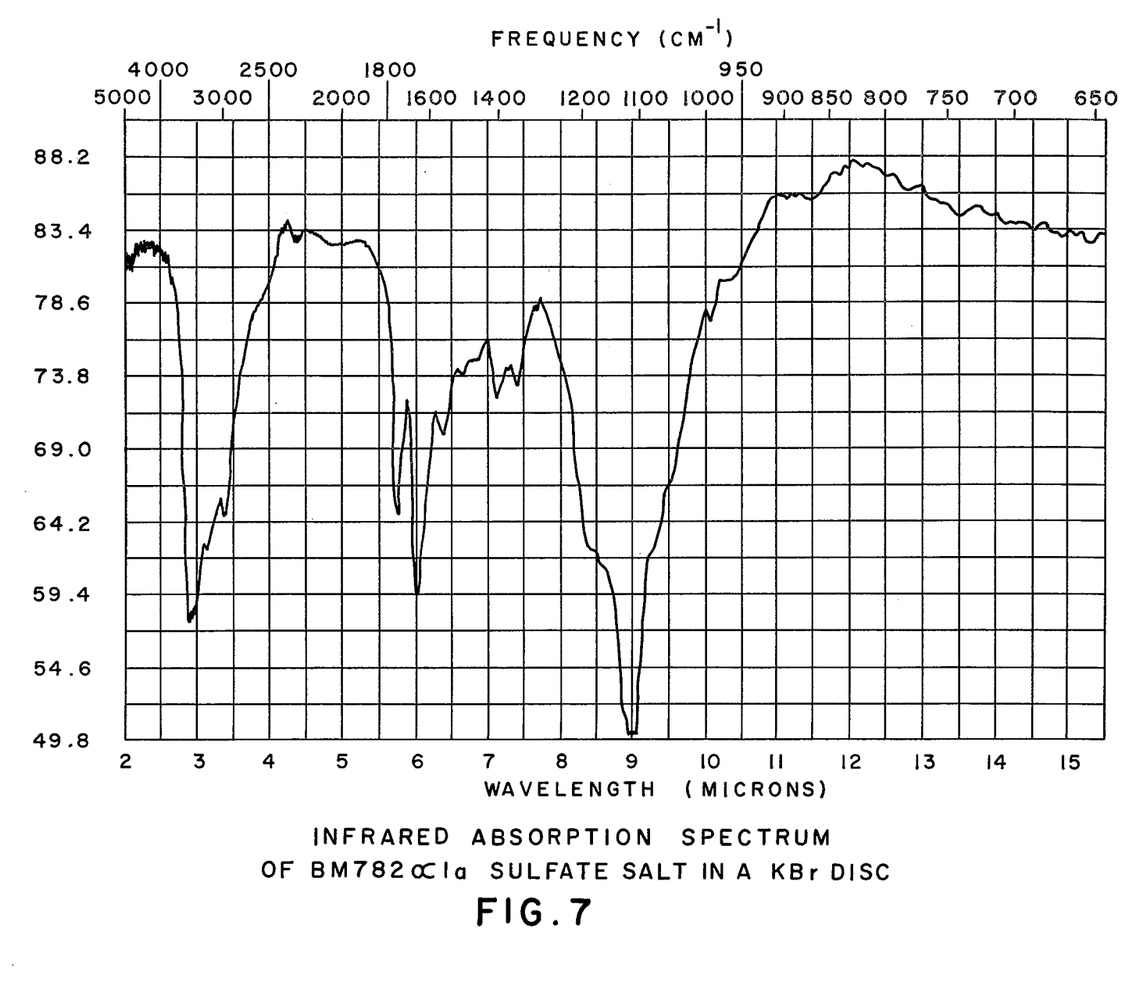

FIG. 7 INFRARED ABSORPTION SPECTRUM OF BM782αIa SULFATE SALT IN A KBr DISC

FIG. 9

PROTON MAGNETIC RESONANCE SPECTRUM OF BM782αIa SULFATE SALT IN D₂O

ANTIBACTERIAL ANTIBIOTIC BM782

CROSS REFERENCE TO RELATED APPLICATIONS

This application is a continuation-in-part of United States Application Ser. No. 891,572, filed Mar. 30, 1978, now abandoned.

BRIEF SUMMARY OF THE INVENTION

This invention relates to three new antibacterial agents designated BM782α1, BM782α2, and BM782α1a; to their production by fermentation; to methods for their recovery and concentration from crude solutions; and to processes for their purification. The present invention includes within its scope the antibiotics in dilute forms, as crude concentrates, and in pure amorphous forms. The effects of the new antibiotics on specific microorganisms, together with their chemical and physical properties, differentiate them from previously described antibacterial agents.

DETAILED DESCRIPTION OF THE INVENTION

The novel antibacterial agents of the present invention are organic bases and thus are capable of forming acid-addition salts with a variety of organic and inorganic salt-forming reagents. The structure of these antibiotics has now been postulated as follows:

[The structure is depicted in the free base form, in a convention which omits showing the acid-addition salt.]

These antibiotics are obtained in the hydrated sulfate salt form. Acid-addition salts can be formed by suitable procedures such as with ion exchange resins with such acids as phosphoric, hydrochloric, hydrobromic, sulfamic, citric, maleic, fumaric tartaric, acetic, benzoic, gluconic, ascorbic, and related acids. The acid-addition salts of the antibacterial agents of the present invention are, in general, solids very soluble in water, slightly soluble in methanol and ethanol but relatively insoluble in non-polar organic solvents such as diethyl ether, benzene, toluene, and the like. For purposes of this invention, the antibacterial free bases are equivalent to their non-toxic acid-addition salts.

The new antibiotics which we have designated BM-782α1, BM782α2, and BM782α1a are formed during the cultivation under controlled conditions of a new strain of an undetermined species of Nocardia. This new antibiotic-producing strain is a mutant derived by gamma radiation of a spore suspension of the parent culture which was isolated from a soil sample collected in Australia. A viable culture of the new microorganism has been deposited with the Culture Collection Laboratory, Northern Regional Research Center, U.S. Dept. of Agriculture, Peoria, Illinois under its accession number NRRL 11,239.

The following is a general description of the microorganism Nocardia sp. NRRL 11,239 based on diagnostic characteristics observed. Observations were made of the cultural, physiological and morphological features of the organism in accordance with the methods detailed by Shirling and Gottlieb, Internat. Journ. of Syst. Bacteriol. 16, 313–340 (1966). The chemical composition of the culture was determined by established procedures.* The underscored descriptive colors and color chip designations were taken from Jacobson et al., Color Harmony Manual, 3rd Edition (1948), Container Corp. of America, Chicago, Ill. Descriptive details are recorded in Tables I through V below.

*Becker et al., Appl. Microbiol. 12, 421–423 (1964) Lechevalier, J. Lab. Clin. Med. 71, 934–944 (1968).

Amount of Growth

Moderate on all media studied except on inorganic salts-starch agar where it was light, and very light on Czapek's solution agar.

Aerial Mycelium

Yellowish to yellowish-white, becoming Light Ivory (2ca) to Pearl Pink (3ca) to Bisque (3ec) in sporulating zones.

Soluble Pigments

Light to moderate in yellowish to yellowish-brown shades.

Reverse Color

In yellowish-brown to brownish shades.

Miscellaneous Physiological Reactions

Complete liquefaction of gelatin; nitrates reduced to nitrites in 7 days; no melanin pigments formed on peptone-iron agar; complete peptonization in purple milk in 14 days; NaCl tolerance in yeast extract agar ≧4% but <7%. Carbon source utilization patterns were determined in Czapek's solution agar, instead of the usual Pridham and Gottlieb [J. Bacteriol., 56, 107–114 (1948)] medium which did not support growth. Results are as follows: Good utilization of d-galactose, glycerol, d(+)mannose, maltose, sucrose, d-trehalose and dextrose; poor to non-utilization of adonitrol, 1-arabinose, d-fructose, i-inositol, lactose, d-mannitol, d-melezitose, d-raffinose and d-xylose.

Chemical Composition

Cell wall and sugar analysis demonstrated that the culture contained meso-2,6-diaminopimelic acid and major amounts of galactose typical of cell wall type IV [Lechevalier (vide supra]; however, atypically, no arabinose was found.

Micromorphology

Aerial mycelium shows varying degrees of segmentation; terminal portions tends to form tangled, branching chains of spore-like elements which disarticulate readily. Spores are globose to elliptical. Spore sheaths dehisce and sheath fragments frequently cling to spores. Spores are 0.3–0.4 μM × 0.5–0.6 μM. Spore surfaces are smooth as determined by transmission electron microscopy at 20,000X.

On the basis of the general characteristics observed, culture NRRL 11,239 appears morphologically to be a representative of the genus Nocardia, i.e. it has the usual segmentation and fragmentation of mycelium and the long chains of disarticulating coccoid spore-like elements. Also, in keeping with the Nocardia concept it shows fastidious utilization of carbon sources and preference for nitrates. Althought the organism was atypical in its lack of arabinose in whole-cell hydrolyzates, this situation is also approached by other Nocardia species [Pridham and Lyons, Devlpmt. Indus. Microbiol., 10, 183–221 (1969)].

According to the McClung system for identification of Nocardia species [Buchanan and Gibbons, Bergey's Manual of Determinative Bacteriology, 8th Edition, Williams and Wilkins Co., Baltimore, Md. (1974)], the culture appears to belong in Morphological Group III; however, it was not readily placed in any of the species categories. Therefore, it is considered an undetermined species of the genus Nocardia.

TABLE I

Cultural Characteristics of Nocardia sp. NRRL 11,239
Incubation: 14 days Temperature: 37° C.

| Medium | Amount of Growth | Aerial Mycelium and/or Spores | Soluble Pigment | Reverse Color |
|---|---|---|---|---|
| Yeast Extract Agar | Moderate | Aerial mycelium yellowish-white, becoming Lt. Ivory (2 ca) in sporulating zones. Sporulation light. | Yellowish; light | Chocolate (5 nl) |
| Asparagine Dextrose Agar | Moderate | Aerial mycelium yellowish-white, becoming Lt. Ivory (2 ca) to Pearl Pink (3 ca) in sporulating zones. Sporulation light. | Yellowish; light | Lt. Spice Brown (4 lg) |
| Benedict's Agar | Moderate | Aerial mycelium yellowish-white, becoming Lt. Ivory (2 ca) in sporulating zones. Sporulation light. | None | Lt. Spice Brown (4 lg) |
| Bennett's Agar | Moderate | Aerial mycelium yellowish, becoming Lt. Ivory (2 ca) to Bisque (3 ec) in sporulating areas. Sporulation light. | Yellowish-brown; moderate | Chocolate (5 po) |
| Inorganic Salts-Starch Agar | Light | Aerial mycelium sparse, yellowish-white, becoming Lt. Ivory (2 ca) to Pearl Pink (3 ca) in sporulating zones. Sporulation light. | None | Whitish |
| Kuster's Oat-flake Agar | Moderate | Aerial mycelium yellowish-white, becoming Pearl Pink (3 ca) in sporulating zones. Sporulation light. | Yellowish; light | Lt. Spice Brown |
| Czapek's Solution Agar | Very light | No aerial mycelium | None | Colorless |
| Potato Dextrose Agar | Moderate | Aerial mycelium yellowish-white, becoming Lt. Ivory (2 ca) in sporulating zones. Sporulation light. | Yellowish; light | Chocolate Brown (5 pn) |
| Tomator Paste Agar | Moderate | Aerial mycelium yellowish-white, becoming Lt. Ivory (2 ca) to Pearl Pink (3 ca) in sporulating areas. Sporulation light. | Yellowish-brown; light | Lt. Spice Brown (4 lg) |
| Pablum Agar | Moderate | Aerial mycelium yellowish-white, becoming Lt. Ivory (2 ca) to Pearl Pink (3 ca) in sporulating areas. Sporulation light. | Yellowish-brown; light | Chocolate (5 nl) |
| Hickey & Tresner's Agar | Moderate | Aerial mycelium yellowish-white, becoming Lt. Ivory (2 ca) in sporulating areas. Sporulation light. | Yellowish; moderate | Chocolate (5 nl) |
| Weinstein's Agar | Moderate | Aerial mycelium yellowish-white; only traces of sporulation. | Yellowish-brown; moderate | Yellow Maple (3 ng) |
| Soil Extract Agar | Moderate | Aerial mycelium yellowish-white, becoming Lt. Ivory (2 ca) in sporulating areas. Sporulation light | None | Chocolate (5 nl) |

TABLE II

Micromorphology of Nocardia sp NRRL 11,239

| Medium | Aerial Mycelium and/or Sporiferous Structures | Spore Shape | Spore Size | Spore Surface |
|---|---|---|---|---|
| Inorganic Salts-Starch Agar | Aerial mycelium shows varying degrees of segmentation; terminal portions tend to form tangled, branching chains of spore-like elements which disarticulate readily. | Globose to elliptical, spore sheaths dehisce & sheath fragments frequently cling to spores | 0.3–0.4μM × 0.5–0.6μM | Smooth as determined by EM at 20,000X |

TABLE III

Miscellaneous Physiological Reaction of Nocardia sp NRRL 11,239

| Medium | Incubation Period | Amount of Growth | Physiological Reaction |
|---|---|---|---|
| Peptone-Iron | 2 days | Moderate | No melanin pigments produced. |
| Gelatin | 7 days | Moderate | Complete liquefaction |
| Purple Milk | 14 days | Moderate | Complete peptonization; no curd. |
| Organic Nitrate Broth | 7 days | Good | Nitrates reduced to nitrites. |
| Yeast extract Agar plus (4, 7, 10 and 13% NaCl) | 14 days | Light | NaCl tolerance ≧4%. <7% |

TABLE IV

Carbon Source Utilization Pattern of Nocardia sp. NRRL 11,239
Incubation: 10 days Temperature: 28° C.

| Carbon Source** | Utilization* | Remarks |
|---|---|---|
| Adonital | 0 | **1% C-source in Czapek's agar |
| l-Arabinose | 0 | |
| d-Galactose | 3 | |
| d-Fructose | 0 | |
| i-Inositol | 0 | |
| Lactose | 0 | |
| d-Mannitol | 0 | |
| d-Melezitose | 1 | |
| Gylcerol | 3 | |
| d-Raffinose | 0 | |
| d(+)Mannose | 3 | |
| Maltose | 3 | |
| Sucrose | 3 | |
| d-Trehalose | 3 | |
| d-Xylose | 0 | |
| Dextrose | 3 | |

TABLE IV-continued

Carbon Source Utilization Pattern of Nocardia sp. NRRL 11,239
Incubation: 10 days Temperature: 28° C.

| Carbon Source** | Utilization* | Remarks |
|---|---|---|
| Negative Control | 0 | |

*3-Good Utilization
1-Poor Utilization
2-Fair Utilization
0-No Utilization

TABLE V

Chemical Composition of Nocardia sp NRRL 11,239

| Cell Wall Type | Major Constituents |
|---|---|
| Type IV | meso-2,6-diaminopimelic acid, galactose |

It is to be understood that for the production of these new antibacterial agents the present invention is not limited to this particular organism or to organisms fully answering the above growth and microscopic characteristics which are given for illustrative purposes only. In fact, it is desired and intended to include the use of mutants produced from this organism by various means such as exposure to X-radiation, ultraviolet radiation, nitrogen mustard, actinophages, and the like. It is also desired and intended to include inter-and intraspecific genetic recombinants produced by genetic techniques known to the art such as conjugation, transformation, transduction, or by genetic engineering techniques.

The antibacterial agents of the present invention were compared in vitro using a variety of gram positive and gram negative bacteria by the standard agar dilution procedure. The results are reported as minimal inhibitory concentrations (mcg./mg.) in Table VI below.

TABLE VI

In vitro Spectrum

| Organism | Minimal Inhibitory Concentration (mcg.ml.) | | |
|---|---|---|---|
| | BM782α1 | BM782α2 | BM782α1a |
| *Escherichia coli* KC-74-1 | 4 | 4 | 64 |
| *Escherichia coli* W-75-1 | 4 | 4 | 128 |
| *Escherichia coli* OSU-75-1 | 4 | 4 | 64 |
| *Escherichia coli* K-77-29 | 16 | 16 | >128 |
| Klebsiella sp KC-74-1 | 4 | 2 | 64 |
| *Klebsiella pneumoniae* W-75-1 | 4 | 2 | 64 |
| Enterobacter sp OSU-75-1 | 2 | 2 | 64 |
| *Proteus morganii* K-72-1 | 4 | 2 | 128 |
| *Proteus rettgeri* N-74-1 | 8 | 4 | >128 |
| Salmonella sp KC-74-1 | 4 | 4 | 64 |
| *Salmonella enteriditis* W-75-1 | 4 | 2 | 64 |
| *Salmonella enteriditis* K-72 | 2 | 2 | 64 |
| *Shigella flexneri* RB | 0.12 | 0.25 | 1 |
| *Shigella flexneri* M42-43 | 0.12 | 0.25 | 1 |
| *Shigella sonnei* 53GX7 | 8 | 4 | 64 |
| Serratia OSU-75-1 | 4 | 2 | 128 |
| Serratia St. Luke P55 | 2 | 2 | 128 |
| Serratia MA-75-1 | 2 | 2 | 128 |
| *Acinetobacter calcoaceticus* MAYO-75-4 | 32 | 32 | 128 |

TABLE VI-continued

| | In vitro Spectrum | | |
|---|---|---|---|
| | Minimal Inhibitory Concentration (mcg.ml.) | | |
| Organism | BM782α1 | BM782α2 | BM782α1a |
| *Acinetobacter calcoaceticus* MAYO-75-10 | 16 | 16 | 128 |
| *Acinetobacter calcoaceticus* AEMC-75-5 | 8 | 8 | 128 |
| *Pseudomonas aeruginosa* PDO5141 | 64 | 64 | 128 |
| *Pseudomonas aeruginosa* 12-4-4 | 32 | 64 | 128 |
| *Staphylococcus aureus* OSU-75-1 | 0.25 | 0.25 | 1 |
| *Staphylococcus aureus* OSU-75-2 | 0.25 | 0.25 | 1 |
| *Staphylococcus aureus* OSU-75-3 | 0.5 | 0.5 | 4 |
| *Klebsiella pneumoniae* AD | 1 | 1 | 8 |
| *Escherichia coli* 311 | 4 | 4 | 128 |

The antibacterial agents BM782α1, BM782α2, and BM782α1a are also active in vivo against a variety of organisms, now found to include *Mycobacterium tuberculosis*. These new antibacterials are thereby useful as therapeutic agents for treating bacterial and tubercular infections in mammals. These new agents can be usefully employed for treating or controlling such infections by parenteral administration. The usefulness of these new antibacterial agents is demonstrated by their ability to control systemic lethal infections in mice. The animals used were Charles River CD-1 strain female mice, approximately 6 weeks old and averaging 20±2 grams in weight. Infections were produced by intraperitoneal injections of a 0.5 ml. volume (lethal dose) of a trypticase soy broth (TSB) dilution of a 5-hour TSB blood culture of the microorganisms listed in Table VII below.

TABLE VII

| Microorganism | TSB Dilution of 5 Hour TSB Culture |
|---|---|
| *Escherichia coli* 311 | 4.2 × 10⁵ |
| *Klebsiella pneumoniae* AE | 1.8 × 10⁴ |

The test compounds were administered in a single 0.5 ml subcutaneous dose in 0.2% aqueous agar 30 minutes after infection, at the indicated dosage levels. The results are set forth in Table VIII as survival ratio (alive/total) at 7 days post infection.

The usefulness of these new agents as anti-tubercular drugs is demonstrated by their ability to control tubercular infections in mice. This was demonstrated by the following procedure:

Carworth Farms CF1 female white mice, 4 to 6 weeks old, weighing 17 to 22 grams are infected with *Mycobacterium tuberculosis* H37Rv by intravenous administration of 0.2 ml. of a buffered saline suspension containing approximately 1.5 mg./ml. wet weight of a 12 to 14 day culture of the test organism grown on Sauton's agar medium. The mice are then segregated in a random manner into cages, each of which holds 2, 5 or 10 mice. Four groups of 5 mice each are retained as infected, untreated controls. The remaining mice are used to determine the activity of the test compounds. The test compounds are administered subcutaneously in ½ ml. aqueous doses at various concentrations in a total of 8 injections spread over 10 days. A compound is considered active if it either saves 35% or more of the mice in a test group, or prolongs the average survival time by 4 or more days compared to infected, untreated controls. Tests are terminated 30 days after the day of infection.

The results of this test of BM782α1 and BM782α2 are given in Table VIIA.

TABLE VIIA

| | Alive/Total Mice Tested 30 Days After Infection | | |
|---|---|---|---|
| Compound | Subcutaneous Dose in mg./kg./day | Summary Alive/Total | Percent |
| BM782α1 | 100 | 22/25 | 88 |
| | 50 | 18/26 | 69 |
| | 25 | 15/37 | 41 |
| BM782α2 | 100 | 8/22 | 36 |
| Infected, Untreated Controls | | 3/50 | 6 |
| Normal Controls | | 25/25 | 100 |

TABLE VIII

| Dose mg./kg. | *Escherichia coli* 311 | | | *Klebsiella pneumoniae* AD | |
|---|---|---|---|---|---|
| | BM782α1 | BM782α2 | BM782α1a | BM782α1 | MB782α2 |
| 16 | 5/5 | 5/5 | 5/5 | 5/5 | 5/5 |
| 8 | 5/5 | 5/5 | 5/5 | 5/5 | 5/5 |
| 4 | 5/5 | 5/5 | 5/5 | 5/5 | 5/5 |
| 2 | 5/5 | 5/5 | 3/5 | 5/5 | 5/5 |
| 1 | 5/5 | 2/5 | 0/5 | 5/5 | 4/5 |
| 0.5 | 1/5 | 1/5 | 0/5 | 5/5 | 4/5 |
| 0.25 | 0/5 | 0/5 | 0/5 | 1/5 | 0/5 |

Fermentation Process

Cultivation of the organism *Nocardia* sp. NRRL 11,239 may be carried out in a wide variety of liquid culture media.

Media which are useful for the production of the novel antibiotics include an assimilable source of nitrogen such as protein, protein hydrolysate, polypeptides, amino acids, corn steep liquor, etc.; an assimilable source of carbon such as starch, sugar, molasses, glycerol, etc.; and inorganic anions and cations, such as potassium, sodium, calcium, sulfate, phosphate, chloride, etc. Trace elements such as boron, molybdenum, copper, etc., are supplied as impurities of other constituents of the media. Aeration in tanks and bottles is provided by forcing sterile air through or onto the surface of the fermenting medium. Further agitation in tanks is provided by a mechanical impeller. An antifoaming agent such as lard oil may be added as needed.

Inoculum Preparation

Shaker flask inoculum of *Nocardia* sp. NRRL 11,239 is prepared by inoculating 100 ml. of sterile liquid medium in 500 ml. flasks with scrapings or washings of the growth from an agar slant of the culture or by adding frozen vegetative seed to the flasks. The following medium is ordinarily used.

| Corn starch | 30 g. |
|---|---|
| Molasses | 20 g. |
| Soy flour | 15 g. |
| Calcium carbonate | 10 g. |
| Water qs | 1 liter |

Frozen vegetative seed is prepared by pipetting 5–10 ml. of vegetative liquid growth into sterile tubes and storing in a freezer at −8° F.

The flasks are incubated at 25°–29° C., preferably 28° C., and agitated vigorously on a rotary shaker for 24–48 hours. These 100 ml. portions of inocula are used to inoculate one liter and 12 liter batches of the same medium in 2 liter and 20 liter glass fermentors. The inoculum mash is aerated with sterile air while growth is continued for 24 to 48 hours. These batches of inocula are used to inoculate tank fermentors.

Tank Fermentation

For the production of the antibiotic in tank fermentors a fermentation medium of the following formulation is preferably used:

| Corn starch | 30 g. |
|---|---|
| Molasses | 20 g. |
| Soy flour | 15 g. |
| Calcium carbonate | 10 g. |
| Water qs | 1 liter |

Each tank is inoculated with 3–10% of its medium volume of inoculum prepared as described above. Aeration is supplied at the rate of 0.4–1.0 liter of sterile air per liter of broth per minute and the fermenting mixture is agitated by an impeller driven at 100–400 r.p.m. The temperature is maintained at 25°–29° C., usually at 28° C. The fermentation is ordinarily continued for 65–90 hours, at which time the mash is harvested based on determinations made using pH, mycelial growth and turbidimetric assay against *K. pneumoniae*.

Isolation Procedure

The harvested mash is combined with sodium fluoride in a ratio of 5 g. per liter of mash and adjusted to pH 6.5. This mixture is filtered through diatomaceous earth and washed with tap water. The combined filtrate and washing is put through a column containing a weak cation exchange resin in the sodium form in an approximate ratio of one liter of resin per 55 gallons of filtrate. The column is washed first with demineralized water and then with an acetate buffer solution. The column is again washed with demineralized water and eluted with 0.36 N sulfuric acid. Elution is continued until the eluate pH is 1.5. The eluate is adjusted to pH 6.5 with barium hydroxide and filtered. The filtrate is again adjusted to pH 6.5 and filtered.

The filtrate is freeze dried providing a solid material. This solid is dissolved in water and chromatographed on a dextran cation exchanger in the sodium form. The column is equilibrated with 1% sodium sulfate at a pH slightly on the acidic side. The column is developed using a gradient of from 1% to 7% sodium sulfate solution. Fractions are collected and the product is detected by using ninhydrin, t-butyl hypochlorite/starch/iodide or Sakaguchi reagents. Based on these color tests the fractions containing BM782α1, and BM782α2, are combined separately. Each combination is passed through a column of granular carbon. The columns are washed free of salt and eluted with a solution of water:acetone (60:40). Each eluate is concentrated and freeze dried, providing essentially pure solid BM782α1 and BM782α2 preparations.

The above procedure will yield antibiotics of the sulfate form. It will be obvious, to those skilled in the art, that the free base or other acid-addition salts may be produced by art recognized methods. Among these methods are performing the elution steps utilizing the desired acid salt as eluent, or passing the above produced sulfate form of the antibiotic through a strong anion exchange resin bearing the desired acid-addition salt.

The invention will be described in greater detail in conjunction with the following specific examples.

EXAMPLE 1

Inoculum Preparation

The medium used to grow the primary inoculum is prepared according to the following formula:

| Corn starch | 30 g. |
|---|---|
| Molasses | 20 g. |
| Soy flour | 15 g. |
| Calcium carbonate | 10 g. |
| Water qs | 1 liter |

Frozen vegetative seed, obtained from a prior inoculum mash inoculated with spores of NRRL 11,239, is used to inoculate two 500 ml. flasks each containing 100 ml. of the above sterile medium. The flasks are placed on a rotary shaker and agitated vigorously for 24 hours at 28° C. The resulting flask inoculum is transferred to a 5 gallon glass fermentor containing 12 liters of the same sterile medium. The glass fermentor is aerated with sterile air while growth is carried out for 48 hours.

EXAMPLE 2

Fermentation

A medium is prepared according to the following formula:

| Corn starch | 30 g. |
|---|---|
| Molasses | 20 g. |
| Soy flour | 15 g. |
| Calcium carbonate | 10 g. |
| Water qs | 1 liter |

This fermentation medium is sterilized at 120° C. with steam at 15 pounds pressure for 45–60 minutes. The pH of the medium after sterilization is 7.1. Three hundred liters of the above sterile medium in a 400 liter tank fermentor is inoculated with 12 liters of inoculum (prepared as described in Example 1) and the fermentation is carried out at 24°–28° C. using Hodag FD82 as a defoaming agent. Aeration is supplied at the rate of 0.4 liter of sterile air/liter of mash/minute. The mash is agitated by an impeller driven at 180–240 r.p.m. At the end of 66–90 hours of fermentation time, the mash is harvested.

EXAMPLE 3

Isolation of BM782α1

A 300 liter portion of harvest mash (prepared as described in Example 2) is combined with 1500 g. of sodium flouride and adjusted to pH 6.5. The mixture is filtered through diatomaceous earth and washed with 40 liters of tap water. The combined filtrate and washings are put through a 5 liter bed of Amberlite ® IRC50 (sodium form) in a 4 inch×60 inch glass column. The column is washed with 20 liters of demineralized water followed by 25 liters of a solution of sodium acetate (8 g./liter) which is adjusted to pH 3.5 with glacial acetic acid. The column is then washed with 20 liters of demineralized water. The column is eluted with 0.36 N sulfuric acid until the pH of the eluate reaches 1.5. The eluate is adjusted to pH 6.5 with barium hydroxide and filtered. The filtrate is readjusted to pH 6.5 with barium hydroxide and filtered (A).

A 300 liter harvest mash from an identical fermentation is treated essentially as described above providing a second filtrate (B). A 2 liter portion of the first filtrate (A) is freeze-dried giving 13.0 g. of material (A). A 7 liter portion of the second filtrate (B) is freeze-dried giving 41.0 g. of material (B).

A 5 g portion of (A) is dissolved in 35 ml. of water and is chromatographed over a 500 ml. column of CM Sephadex C25 (sodium form) which is equilibrated with 1% sodium sulfate solution at pH 6.7. The column is developed using a gradient of 1-7% sodium sulfate solution. Fractions of 70 ml. each are collected from the column. The fractions are tested by color reagents such as ninhydrin, to determine which contain BM782α1. These fractions (100-112) are combined and passed through a column containing 50 ml. of granular carbon slurry. The column is washed with 2 liters of water and then eluted with 800 ml. of water:acetone (60:40) solution adjusted to pH 4.5 with dilute sulfuric acid. The acid eluate is concentrated and freeze-dried giving 479 mg. of BM782α1 as a hydrated sulfate salt.

A 6.0 g. portion of (B) is treated in the same manner, combining fractions 85-97, passing them through a column containing a 60 ml. slurry of granular carbon, washing the column with one liter of water and eluting as above giving 500 mg. of BM782α1 as a hydrated sulfate salt. The two products are combined giving 979 mg. of BM782α1 as a white solid material. (C, 31.79; H, 6.18; N, 12.48; S, 7.40); specific rotation 0° when measured at a concentration of 0.48% in water.

Figure 1:
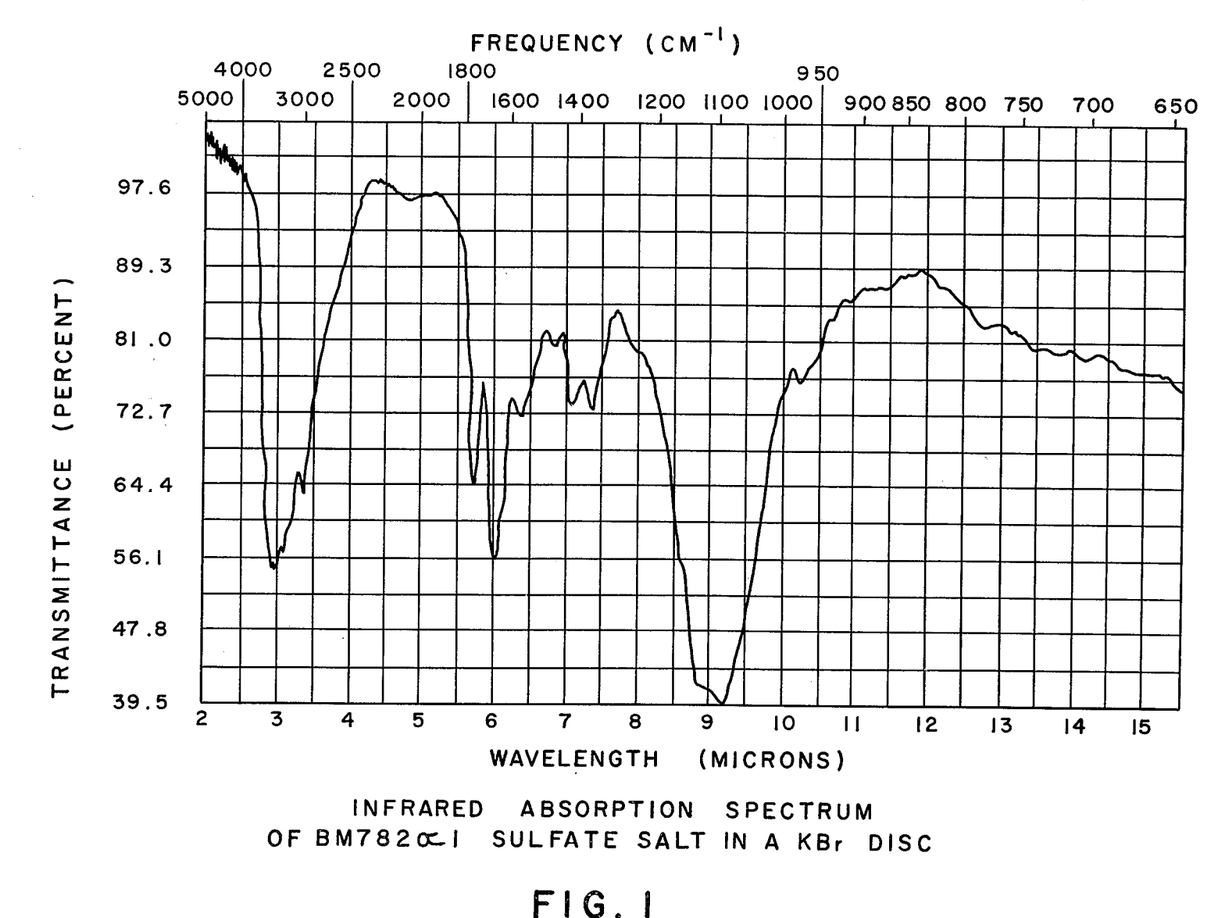
Figure 3:
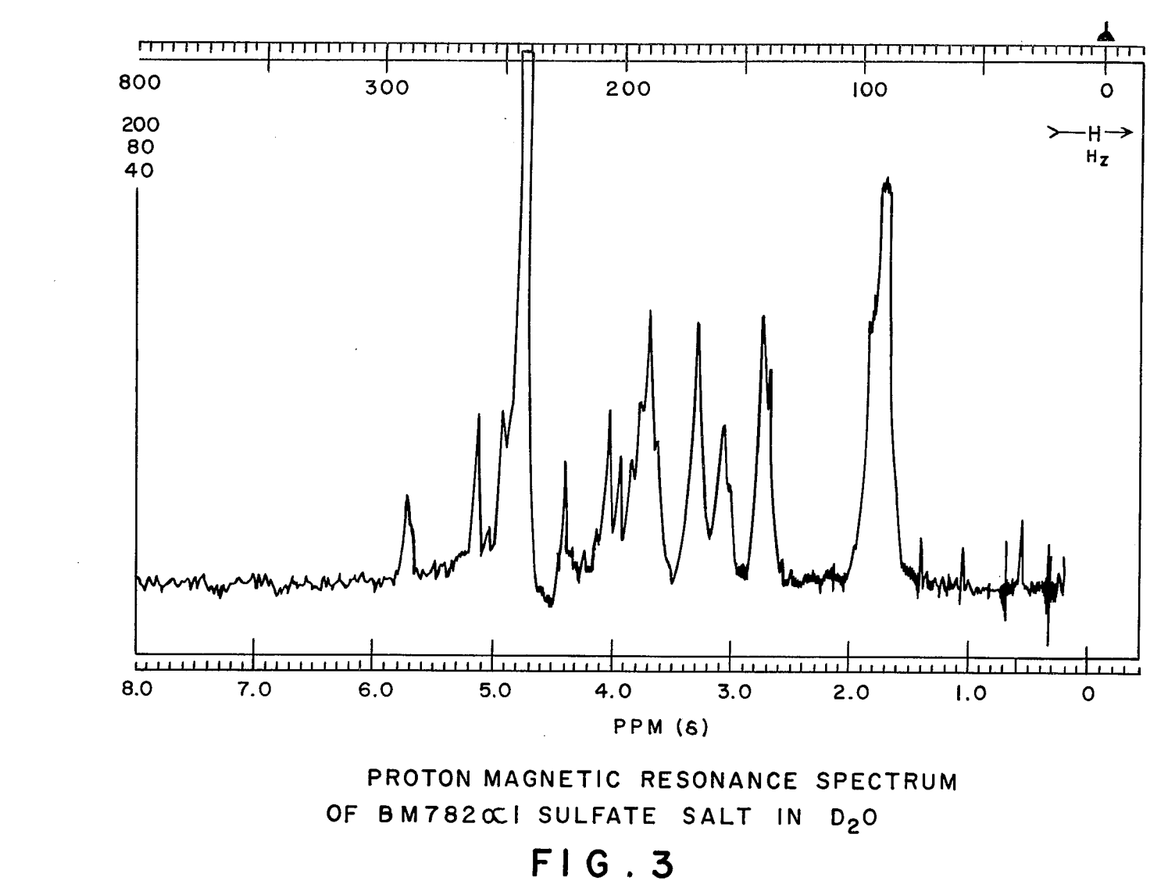

A standard infrared absorption spectrum of the sulfate salt of BM782α1 prepared in a KBr pellet is shown in FIG. 1 of the accompanying drawings. A standard $^{13}C$ nuclear magnetic resonance spectrum of the sulfate salt of BM782α1 is shown in FIG. 2 of the accompanying drawings. A standard proton magnetic resonance spectrum of the sulfate salt of BM782α1 is shown in FIG. 3 of the accompanying drawings.

EXAMPLE 4

Isolation of BM782α2

The procedure of Example 3 is repeated giving a 6.0 g. portion of (A) and a 6.0 g. portion of (B). The 6.0 g. of (A) is dissolved in 35 ml. of 1% sodium sulfate solution and chromatographed as described in Example 3. The 60 ml. fractions containing BM782α2 are identified by spray reagents such as ninhydrin (60-79) and combined and eluted from the carbon column at pH 4.4. The freeze-dried product weighs 660 mg. The 6.0 g. of (B) is dissolved in 35 ml. of water and treated as described in Example 3 giving 515 mg. of product. The two products are combined giving 1.15 g. of BM782α2 hydrated sulfate as a white solid (C, 31.31; H, 6.16; N, 12.04; S, 7.31); specific rotation 0° when measured at a concentration of 0.68% in water.

Figure 4:
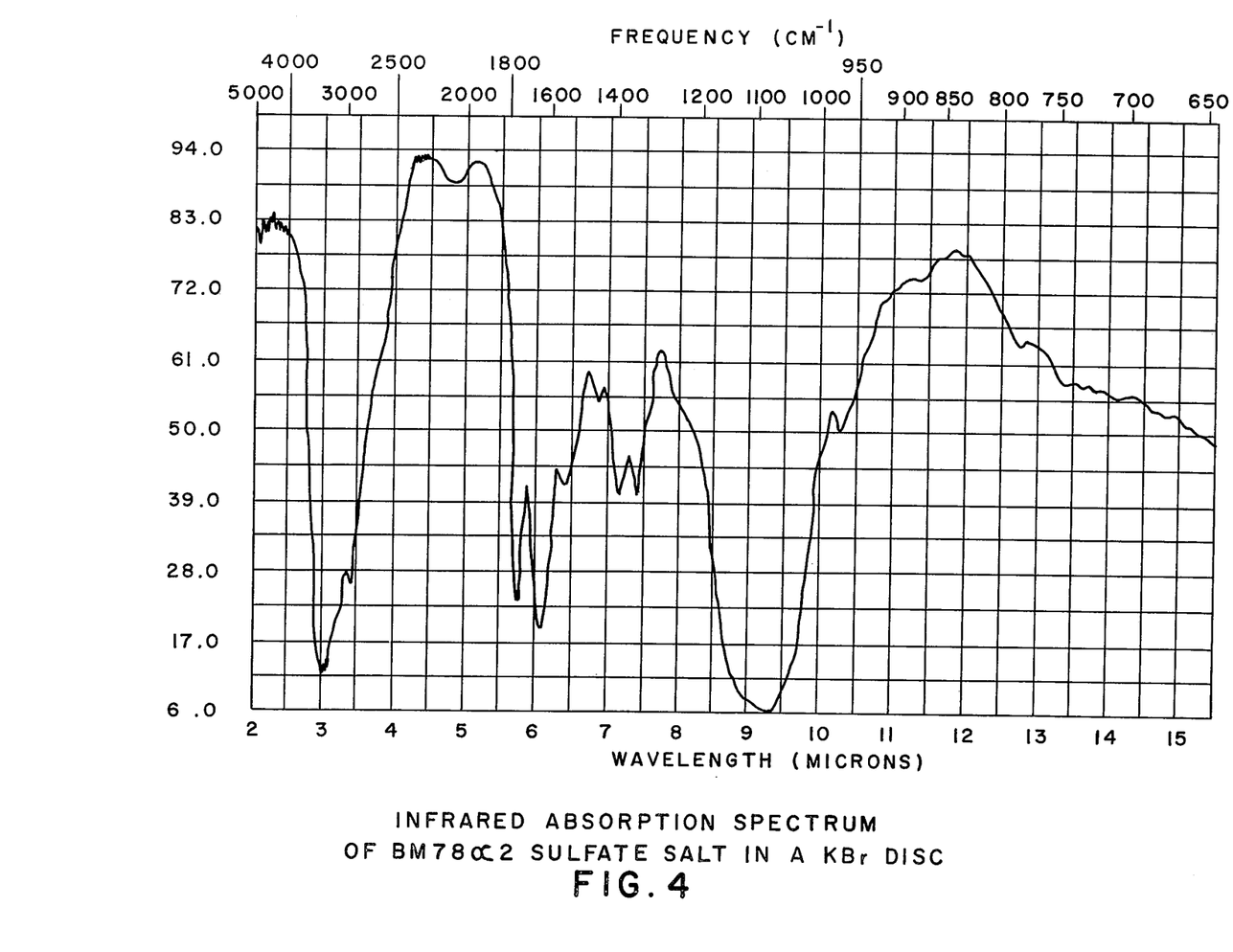
Figure 5:
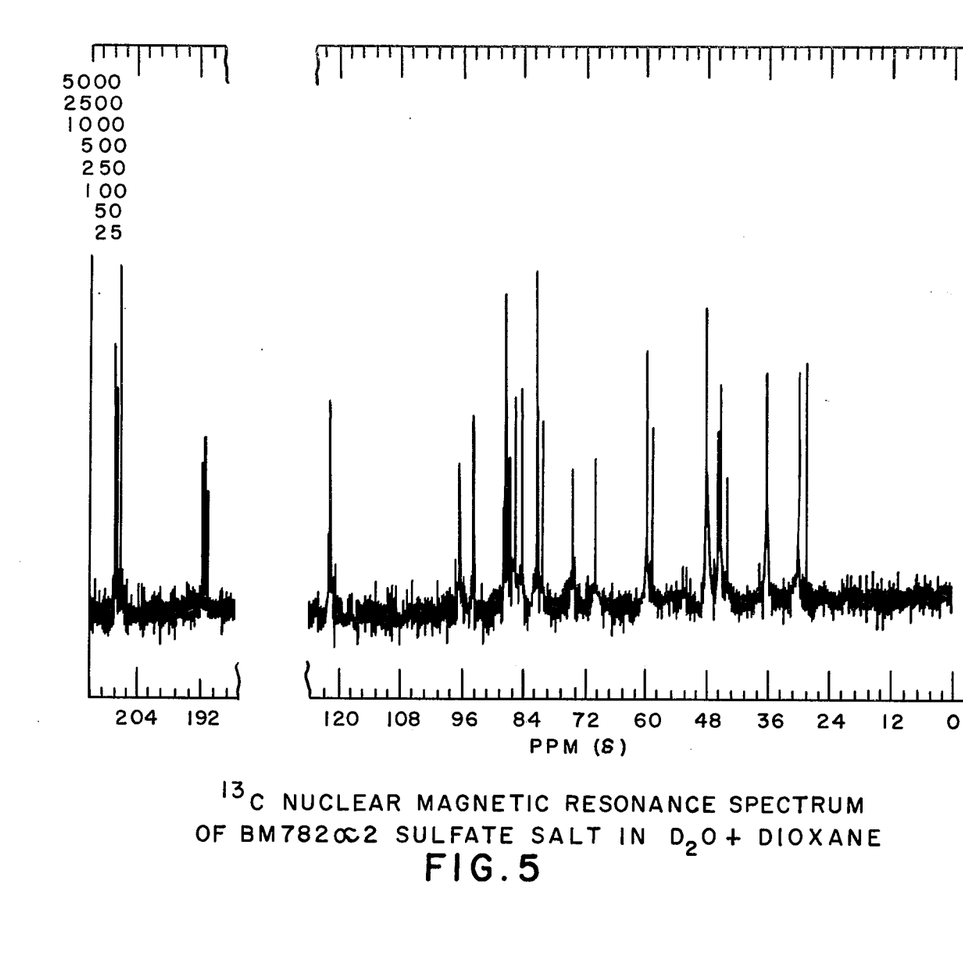
Figure 6:
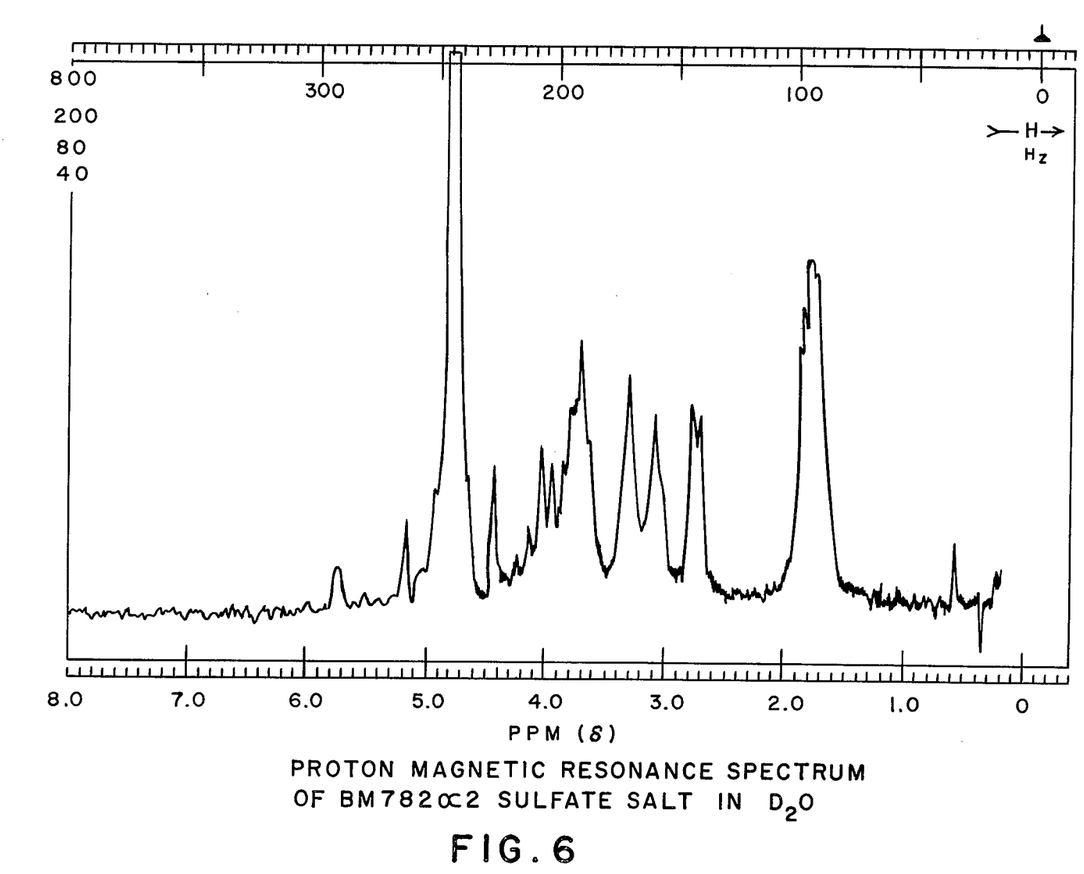

A standard infrared absorption spectrum of the sulfate salt of BM782α2 prepared in a KBr pellet is shown in FIG. 4 of the accompanying drawings. A standard $^{13}C$ nuclear magnetic resonance spectrum of the sulfate salt of BM782α2 is shown in FIG. 5 of the accompanying drawings. A standard proton magnetic resonance spectrum of the sulfate salt of BM782α2 is shown in FIG. 6 of the accompanying drawings.

EXAMPLE 5

Isolation of BM782α1a

A 300 liter portion of harvest mash is combined with 1500 g. of sodium fluoride and adjusted to pH 6.5. The mixture is filtered through diatomaceous earth and washed with 40 liters of tap water. The combined filtrate and washings are put through a 5 liter bed of Amberlite ® IRC 50 (sodium form) in a 4 inch×60 inch glass column. The column is washed with 20 liters of demineralized water followed by 25 liters of a solution of sodium acetate (8 g./liter) which is adjusted to pH 3.5 with glacial acetic acid. The column is then washed with 20 liters of demineralized water. The column is eluted with 0.36 N sulfuric acid until the pH of the eluate reaches 1.5. The eluate is adjusted to pH 6.5 with barium hydroxide and filtered. The filtrate is readjusted to pH 6.5 with barium hydroxide and filtered.

A 2 liter portion of this filtrate is freeze-dried, giving 13.0 g. of solid. A 5.0 g. portion of this solid is dissolved in 35 ml. of water and chromatographed over a 500 ml. column of CM Sephadex C25 (sodium form) which is equilibrated with 1% sodium sulfate solution at pH 6.7. The column is developed using a gradient of 1-7% sodium sulfate solution. Fractions of 70 ml. each are collected from the column. The fractions are tested by color reagents such as ninhydrin, to determine which contain BM782α1a. These fractions (115-120) are combined and passed through a column containing 50 ml. of granular carbon slurry. The column is washed with 2 liters of water and then eluted with 800 ml. of water:acetone (60:40) solution adjusted to pH 4.5 with dilute sulfuric acid. The acid eluate is concentrated and freeze-dried giving 43 mg. of BM782α1a as a hydrated sulfate salt, having a specific rotation +4°±2° when measured at a concentration of 0.653% in water and an analysis C, 30.18; H, 6.16; N, 11.76; S, 8.61.

Figure 8:
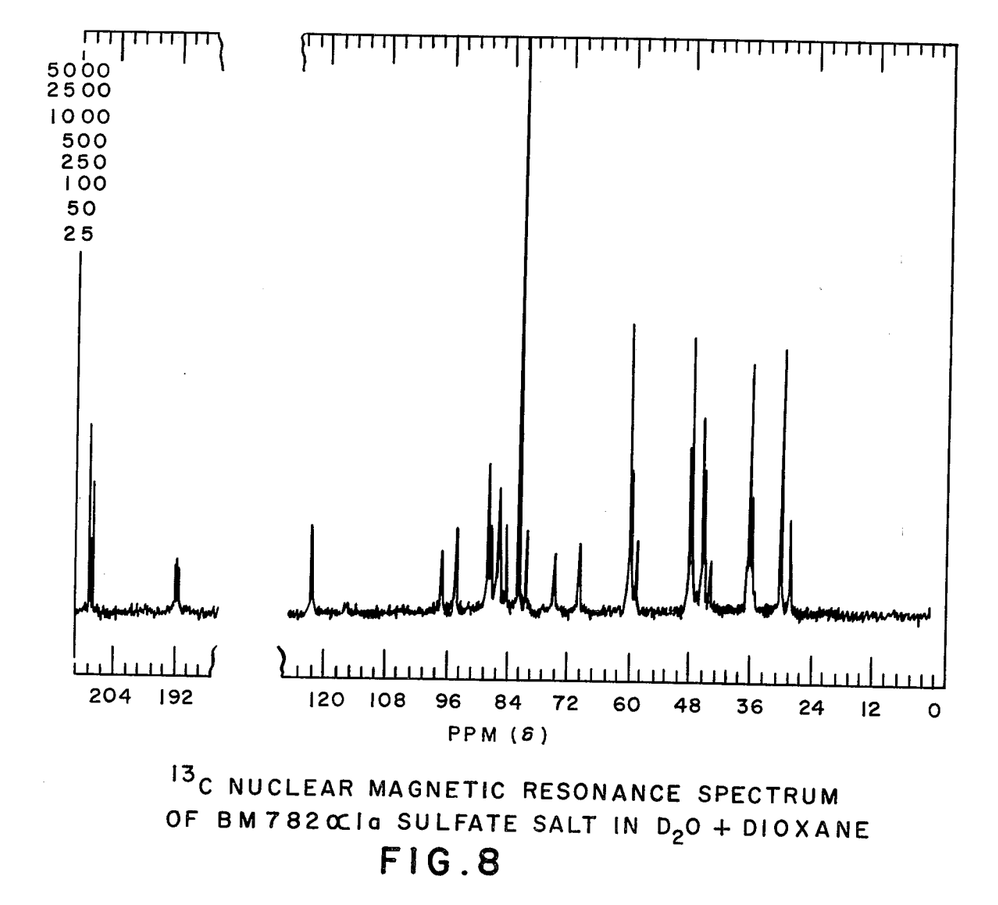
Figure 9:
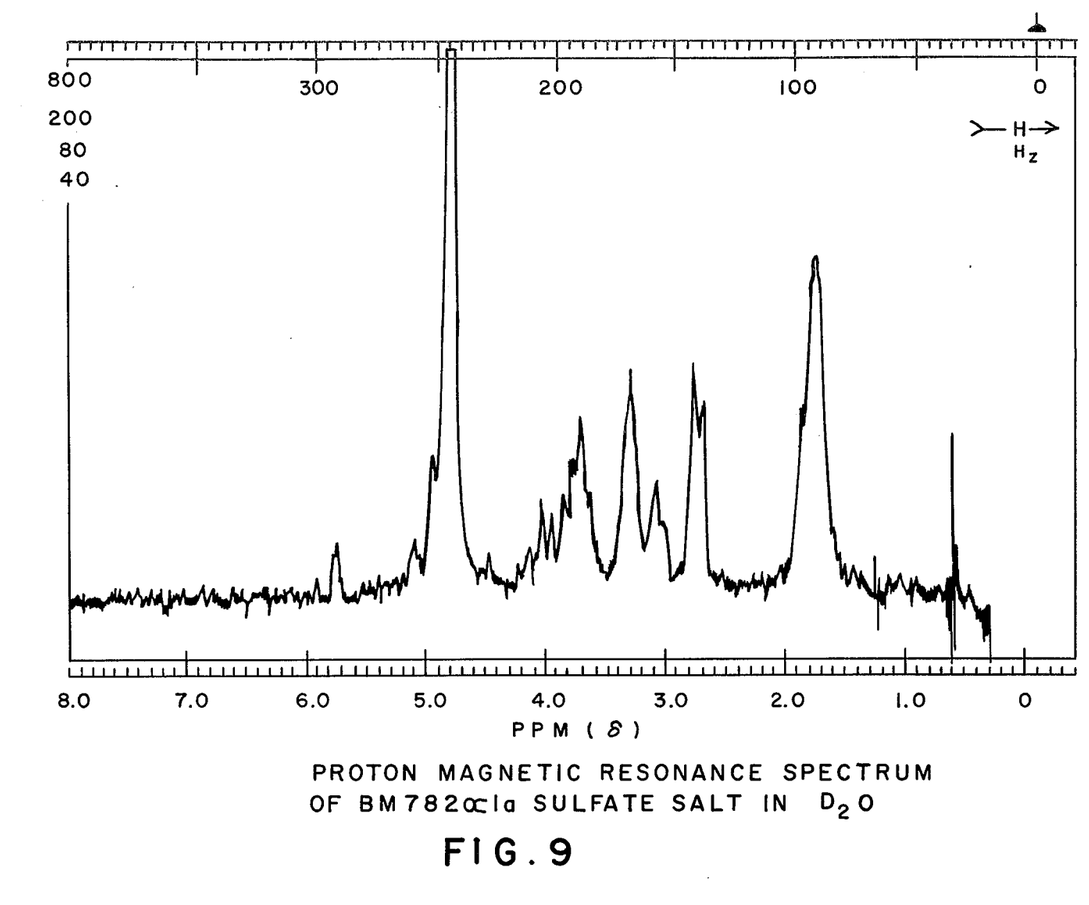

A standard infrared absorption spectrum of the sulfate salt of BM782α1a prepared in a KBr pellet is shown in FIG. 7 of the accompanying drawings. A standard $^{13}C$ nuclear magnetic resonance spectrum of the sulfate salt of BM782α1a is shown in FIG. 2 of the accompanying drawings. A standard proton magnetic resonance spectrum of the sulfate salt of BM782α1a is shown in FIG. 9 of the accompanying drawings.

We claim:

1. Antibiotic BM782α1 which
   (a) is effective as an antibacterial agent; and in its essentially pure amorphous sulfate form;
   (b) has the following elemental analysis (percent): C, 31.79; H, 6.18; N, 12.48; S, 7.40;
   (c) has an optical rotation $[\alpha]_D^{20}=0°$ (C-0.48 in water);
   (d) has an infrared absorption spectrum as shown in FIG. 1 of the drawings;

(e) has a characteristic $^{13}$C nuclear magnetic resonance spectrum as shown in FIG. 2 of the drawings;

(f) has a characteristic proton magnetic resonance spectrum as shown in FIG. 3 of the drawings; and (g) has a structure of and acid-addition salts thereof.

2. Antibiotic BM782α2 which (a) is effective as an antibacterial agent; and in its essentially pure amorphous sulfate form;

(b) has the following elemental analysis (percent): C, 31.31; H, 6.16; N, 12.05; S, 7.31;

(c) has an optical rotation $[\alpha]_D^{20}=0°$ (C–0.68 in water);

(d) has an infrared absorption spectrum as shown in FIG. 4 of the drawings;

(e) has a characteristic $^{13}$C nuclear magnetic resonance spectrum as shown in FIG. 5 of the drawings;

(f) has a characteristic proton magnetic resonance spectrum as shown in FIG. 6 of the drawings; and (g) has a structure of and acid-addition salts thereof.

3. Antibiotic BM782α1a which (a) is effective as an antibacterial agent; and in its essentially pure amorphous sulfate form;

(b) has the following elemental analysis (percent): C, 30.18; H, 6.16; N, 11.76; S, 8.61;

(c) has an optical rotation $[\alpha]_D^{20}=+4°\pm2°$ (C=0.653 in water);

(d) has an infrared absorption spectrum as shown in FIG. 7 of the drawings;

(e) has a characteristic $^{13}$C nuclear magnetic resonance spectrum as shown in FIG. 8 of the drawings;

(f) has a characteristic proton magnetic resonance spectrum as shown in FIG. 9 of the drawings; and has a structure of and acid-addition salts thereof.

* * * * *